US012667579B2

(12) United States Patent
Bourezg et al.

(10) Patent No.: US 12,667,579 B2
(45) Date of Patent: Jun. 30, 2026

(54) PHARMACEUTICAL COMPOSITIONS FOR CLINICAL NUTRITION

(71) Applicants: BAXTER INTERNATIONAL INC., Deerfield, IL (US); BAXTER HEALTHCARE SA, Glattpark (CH)

(72) Inventors: Zouaoui Bourezg, Braine-l'Alleud (BE); Cyrille Pousset, Brussels (BE)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 513 days.

(21) Appl. No.: 17/332,499

(22) Filed: May 27, 2021

(65) Prior Publication Data

US 2022/0395516 A1 Dec. 15, 2022

(51) Int. Cl.

*A61K 31/661* (2006.01)
*A61K 9/00* (2006.01)
*A61L 2/04* (2006.01)
*A61P 3/02* (2006.01)
*A61P 3/12* (2006.01)
*A61L 103/05* (2026.01)

(52) U.S. Cl.

CPC .......... *A61K 31/661* (2013.01); *A61K 9/0029* (2013.01); *A61L 2/04* (2013.01); *A61L 2103/05* (2026.01)

(58) Field of Classification Search

CPC ....... A61K 31/661; A61K 9/0029; A61P 3/02; A61P 3/12

See application file for complete search history.

(56) References Cited

U.S. PATENT DOCUMENTS 4,576,930 A 3/1986 Sugiyama et al.

FOREIGN PATENT DOCUMENTS

| | | | |
|---|---|---|---|
| CN | 1517093 | | 8/2004 |
| CN | 1517093 A | * | 8/2004 |
| CN | 101575348 A | | 11/2009 |
| CN | 101851252 | | 10/2010 |
| CN | 104163827 A | | 11/2014 |
| CN | 105732700 | | 7/2016 |
| CN | 111961077 | | 11/2020 |
| EP | 2389348 | | 11/2017 |
| RO | 114618 | | 6/1999 |
| RU | 1667364 | | 3/1995 |
| WO | 2010/080969 A1 | | 7/2010 |

OTHER PUBLICATIONS

Fresenius Kabi, 2019, Australian product information—Glycophos® (Sodium Glycerophosphate), Retrieved from the Internet: https://www.fresenius-kabi.com/au/documents/Glycophos_PI.pdf. (Year: 2019).*

De Oliveira et al., "Aluminum content in Intravenous solutions for administration to neonates: Role of Product preparation and administration method", JPEN (2010), 34 (3), pp. 322-328 (Year: 2010).*

English translation of the claims of Chinese Patent Publication CN-1517093-A (Year: 2023).*

English translation of the description of Chinese Patent Publication CN-1517093-A (Year: 2023).*

International Search Report and Written Opinion for Application No. PCT/US2022/030674 dated Apr. 21, 2023 (31 pages).

Wang et al, Pediatrics & Neonatology (2020). 61(3): 331-337).

Huston et al, Clinical Research (2017), 32(2):266-270.

Hernández-Sánchez et al., European Journal of Clinical Nutrition (2013) 67:230-238.

Mirtallo, Journal of Parenteral and Enteral Nutrition (2010), 34(3):346-347.

Hall et al, Journal of Parenteral and Enteral Nutrition (2017), 41(7):1228-1233.

International Search Report and Written Opinion for Application No. PCT/US2022/030674 dated Dec. 1, 2022 (124 pages).

Fresenius Kabi Ab: "Summary of Product Characteristics: Glycophos Concentrate for Infusion Solutions", Jun. 11, 2007 (Jun. 11, 2007), XP055958152, Retrieved from the Internet: URL:https://www.fresenius-kabi.com/cl/documents/SPC_GLYCOPHOS.pdf [retrieved on Sep. 5, 2022] the whole document.

De Oliveira Sandra R. et al: "Aluminum Content in Intravenous Solutions for Administration to Neonates : Role of Product Preparation and Administration Methods", JPEN—Journal of Parenteral and Enteral Nutrition, vo1. 34, No. 3, May 1, 2010 (May 1, 2010), pp. 322-328, XP055958153, us, ISSN: 0148-6071, DOI: 10.1177/0148607110362531 Retrieved from the Internet: URL:http://journa1s.sagepub.com/doi/fu11-x.

European Third-Party Observations for Appl No. 22732755.8 dated Oct. 31, 2024, 12 pages.

Sandra R. De Oliveira et al., "Aluminum Content in Intravenous Solutions for Administration to Neonates: Role of Product Preparation and Administration Methods" Journal of Parenteral and Enteral Nutrition, vol. 34, No. 3, May 2010, pp. 322-328.

21 CFR 201.323, Aluminum in large and small volume parenterals used in total parenteral, Oct. 18, 2024, 2 pages.

Pharmacopoeia of the People's Republic of China, vol. II, Chinese Pharmacopoeia Commission, 2020, 3 pages.

Machine translation of CN105732700B, Method for preparing beta-sodium glycerophosphate, 7 pages.

Machine translation of CN1517093A, Sodium glycerophosphate injection and its manufacturing method and application, 6 pages.

European Office Action for Appl No. 22 732 755.8-1109 dated Nov. 13, 2024, 8 pages.

(Continued)

*Primary Examiner* — Kamal A Saeed
*Assistant Examiner* — Sagar Patel
(74) *Attorney, Agent, or Firm* — K&L Gates LLP

(57) ABSTRACT

The present disclosure relates to a pharmaceutical composition for providing phosphorus to an adult or pediatric patient, wherein the composition is an aqueous solution of sodium glycerophosphate which by virtue of an improved process for producing the active pharmaceutical ingredient and the pharmaceutical composition is characterized by a low amount of free phosphate, a low amount of SGP-related substances and by a low amount of aluminum. The pharmaceutical composition is used in clinical nutrition, preferably in the preparation of nutritional formulations by compounding. The compositions can further be used for preventing or correcting phosphorus deficiency (hyperphosphatemia) in said adult or pediatric patients.

27 Claims, 6 Drawing Sheets

(56) References Cited

OTHER PUBLICATIONS

European third-party observations for European patent publication No. EP 4346839 dated Dec. 9, 2024, 7 pages.
Machine Translation of CN 105732700B.
European Third-Party Observation for application No. EP20220732755 dated Dec. 2, 2024, 3 pages.
European Notice of Allowance for European Appl No. 22 732 755.8-1109 dated Feb. 14, 2025, 55 pages.
Opposition against European Patent No. 4346839 B1 dated Dec. 22, 2025.
Statement of Facts and Arguments in support of opposition against European Patent No. 4346839 B1 dated Dec. 23, 2025.
Consolidated List of cited opposition documents—European Application No. 22732755.8.
Fresenius Kabi Ab: New Zealad Data Sheet, Retrieved from https://www.fresenius-kabi.com/content/dam/fresenius-kabi/nz/products/product-documents/parenteral-nutrition/Glycophos_Datasheet.pdf.coredownload.inline.pdf.
Extract from the Federal Register, vol. 66, No. 18, Rules and Regulations, p. 7864 (published on Jan. 26, 2001).
Jiben Roy, Pharmaceutical Impurities—A Mini-Review, AAPS PharmSciTech 2002; 3 (2) article 6 (published on Oct. 4, 2002).
Wikipedia: Yield (chemistry), Retrieved from https://en.wikipedia.org/wiki/Yield_(chemistry).
Wikipedia: Chemistry purity, Retrieved from https://en.wikipedia.org/wiki/Chemical_purity.
Merkblatt 914 Nichtrostender Stahl—wenn die Gesundheit zahlt, Informationsstelle Edelstahl Rostfrei (published in 2009).
Journal of Pharmacy and Pharmacology, 1949, vol. 1 (1), pp. 869-876, British Pharmaceutical Conference Blackpool, “Sodium and Calcium Glycerophosphates A Survey”, J.S. Toal and J.I. Philips.
English translation of CN101851252A Table 1.
Journal of the Chemical Society, Transactions, 1914, vol. 105, pp. 1238-1259, “CXV.—The Constitution of the Glycerylphosphates. The synthesis of a- and 13-Glycerylphosphates”, H. King and F. Lee Pyman.
Journal of the American Chemical Society, 1966, 88: 18, “The Crystal and Molecular Structure of Disodium β-Glycerophosphate Pentahydrate (Na2PO4C3H5(OH)2•5H20)”, UI-Haque and Caughlan.
Sigma Aldrich, certificate of analysis for rac-glycerol 1-phosphare sodium salt, dated May 19, 2021.
Fresenius Kabi Ab: “Summary of Product Characteristics: Glycophos Concentrate for Infusion Solutions”.
De Oliveira Sandra R. et al., “Aluminum Content in Intravenous Solutions for Administration to Neonates: Role of Product Preparation and Administration Methods”, Journal of Parenteral and Enteral Nutrition: vol. 34 No. 3, May 2010, 7 pages.
European Search Report for Appl No. 24210283.8-1109 dated Apr. 28, 2025, 18 pages.

* cited by examiner

PHARMACEUTICAL COMPOSITIONS FOR CLINICAL NUTRITION

The invention relates to the field of medical IV solutions, specifically for use in clinical nutrition, corresponding pharmaceutical compositions and nutritional solutions, as well as methods of preparing the same.

The invention relates to pharmaceutical compositions or medical products for providing phosphorus to an adult or a pediatric patient, wherein the composition is an aqueous solution of sodium glycerophosphate(SGP) which is characterized by a low amount of free phosphate, by a low amount of SGP-related substances and by a low amount of aluminum. The pharmaceutical compositions are used in clinical nutrition, preferably in the preparation of nutritional formulations by compounding. The compositions can further be used for preventing or correcting phosphorus deficiency (hyperphosphatemia) in said adult or pediatric patients.

In certain embodiments of the invention, the pharmaceutical compositions of the invention comprise free phosphate in an amount of not more than 5% of the total phosphate and aluminum in an amount of not more than 500 ppb, preferably not more than 400 ppb. The pharmaceutical compositions of the invention, in certain embodiments of the invention, comprise SGP-related products in an amount of less than 15% of the total phosphate.

BACKGROUND OF THE INVENTION

Parenteral nutrition (PN) aims to supply nutrients to patients by venous access. Nutrients are composed of macronutrients (lipids, amino acids or proteins and dextrose or carbohydrates), micronutrients (vitamins and trace elements) and electrolytes.

Parenteral nutrition, such as in the form of one or more solutions, can be provided in the form of flexible bags either in the form of flexible bags containing glucose, amino acids and/or lipids with or without electrolytes in pre-determined concentrations in mono- or multi-chamber bags (MCBs) containing said formulations, respectively. In the case of MCBs the formulations are provided in two, three or more chambers the content of which can be mixed together prior to administration, optionally after addition of further compounds or drugs which are not comprised in the formulations. Alternatively, parenteral nutrition formulations can be obtained by preparing or compounding parenteral nutrition solutions according to an individual prescription for a patient under sterile conditions. PN compounding at large institutions is now largely automated using volumetric pump systems, so-called automated compounding devices (ACDs) to compound the PN formulations. These devices can be used to customize a PN prescription for each patient. It is possible to use ACDs to compound two-in-one PN bags that contain amino acids, dextrose and other additives in one bag, or three-in-one PN bags that contain amino acids, dextrose, additives, and fat all in one bag. Some pharmacies will compound both types and will infuse IVFE (intra-venous fat emulsions) as a separate infusion with two-in-one PNs. This strategy is often used for pediatric patients. It is also possible to administer phosphate outside of parenteral nutrition, e.g., in cases where parenteral nutrition is not needed but patients suffer from hyperphosphatemia. In this case, a phosphate compound can be diluted in or added to a solution for infusion, such as, for example, 0.9% w/v sodium chloride and glucose 5% w/v solution for infusion before administering it to the patient in need.

One of the critically important micronutrients which can be compounded into a solution for infusion or a parenteral nutrition formulation is phosphate. This is especially the case for pediatric patients, such as pre-term infants and neonates, who have a rapid bone growth rate and who without appropriate levels of phosphate and calcium cannot maintain appropriate bone accretion and are at risk of developing metabolic bone disease, leading to osteomalacia, fractures and impaired linear growth. For example, parenterally fed pre-term infants and neonates require large amounts of calcium and phosphate, but in a low volume of solution. However, the lower the volume of solution, the higher is the possibility of precipitation of calcium hydrogen phosphate ($CaHPO_4$). Precipitation could cause, for example, respiratory distress and pulmonary embolism and must absolutely be avoided (Zenoni and Loiacono, European Journal of Hospital Pharmacy (2018), 25(1): 38-42).

It is known that in contrast to standard calcium salts such as, for example, calcium chloride, calcium gluconate can be used as a calcium source. Sodium phosphate or potassium phosphate can thus be used in combination with calcium gluconate to significantly reduce the risk of precipitation of calcium hydrogen phosphate. It has also been suggested to combine calcium gluconate and sodium glycerophosphate to address the issue of precipitation in parenteral nutrition (PN) formulations (Wang et al, Pediatrics & Neonatology (2020). 61(3): 331-337), and SGP is indeed the main organic source of phosphate used in PN products outside the United States, such as, for example, Numeta and Olimel (Baxter).

However, it is known that calcium gluconate, especially if stored or provided in glass vials (CaGluc-Gl), contains significantly higher amounts of aluminium (Al) compared to, for example, solutions made with calcium chloride ($CaCl_2$)), see Huston et al, Clinical Research (2017), 32(2): 266-270. Accordingly, while calcium chloride contains about 2500 mcg/L of Al, calcium gluconate contains about 9500 mcg/L of Al. It could be shown by Huston et al that the aluminium content can be lowered when providing calcium gluconate in plastic bags (CaGluc-Pl), but it is still higher than what should be targeted to reduce aluminium in the final PN formulations. Accordingly, aluminium remains a concern and solutions for this problem are required.

In this context, when comparing aluminium contents in various products, care should be taken to differentiate between the generally concentrated pharmaceutical compositions comprising SGP which are provided mainly for compounding of PN formulations, and (ready-to-use) parenteral nutrition products which contain SGP at generally much lower concentrations. In the context of the present invention, the expressions “pharmaceutical composition(s)” and “medical product(s)” which are interchangeably used herein, refer to such concentrated SGP solutions for injection and use in the preparation of or addition to solutions for infusion or parenteral nutrition solutions for administration to a patient in need. They are generally not intended for direct administration to a patient.

As summarized in Hernández-Sánchez et al., European Journal of Clinical Nutrition (2013) 67:230-238, aluminum (Al) toxicity in parenteral nutrition solutions has been known for a long time and is still unresolved, as many medical products used to compound parenteral nutrition formulations contain Al as a contaminant or as a component of the raw materials. Generally, aluminum is not taken up by the body in large amounts when ingested orally or enterally due to the gastrointestinal tract which allows only <1% of ingested aluminum to reach the blood stream (Hernández-Sánchez et al. (2013)).

Things look different when the GI tract is bypassed, such as in parenteral nutrition. Aluminum tends to accumulate in the body, such as in bones, the liver and CNS, but also in the spleen and the kidneys. For example, aluminum seems to interfere with and impair the kidneys, especially in neonates with an immature renal function, patients with an established renal impairment, including patients suffering from acute or chronic kidney failure and/or elderly and geriatric patients with a normal, age related reduced renal function, such as, for example, patients older than about 40, about 50 or about 60 and especially older than about 70 years of age. Other patients having an increased risk may be burn patients or plasmapheresis patients, as well as other patients having received higher amounts of albumin (see also Hernández-Sánchez, 2013). Other manifestations of Al toxicity summarized again in Hernández-Sanchez et al. (2013) are neurodegenerative disorders (e.g., dialysis encephalopathy, progressive dementia, impaired neurological development, Alzheimer's disease and Parkinson's disease); metabolic bone disease (e.g., bone pain, proximal muscle weakness, multiple nonhealing fractures, premature osteoporosis, osteopenia and osteomalacia); microcytic anemia and cholestasis. Al may further have a hepatotoxic effect, causing, for example, hepatic hemorrhage and necrosis of hepatocytes.

The matter of aluminum toxicity has at least been addressed in the United States by the ASCN, the ASPEN working group and the FDA, that has issued a rule governing Al content in large volume pharmaceutical compositions as well as in small volume pharmaceutical compositions used to prepare parenteral nutrition solutions. This includes FDA recommendations or guidelines asking for <5 mg/kg/day using current pharmaceutical products to compound PN solutions. However, technical obstacles have so far reduced the ability to provide low aluminum medical products, including low aluminum sodium glycerophosphate solutions for use in clinical nutrition. Hernández-Sánchez et al. (2013), in consequence, note that "calcium and phosphorus intakes would need to be eliminated or substantially decreased in order to limit the Al load presented by PN", see also Mirtallo, Journal of Parenteral and Enteral Nutrition (2010), 34(3):346-347.

As mentioned before (Anderson, Journal of Parenteral and Enteral Nutrition (2016), 40(8):1166-1169), calcium gluconate is preferred over calcium chloride when compounding PN because of its superior compatibility with inorganic phosphates. PN solutions containing calcium gluconate carry a higher aluminium load than equivalent solutions compounded with calcium chloride, leading to increased potential for aluminium toxicity. Importantly, SGP has a lower propensity to precipitate with the divalent calcium ion than inorganic phosphate, allowing for calcium chloride utilization. Accordingly, SGP and calcium chloride compatibility provide a clinical option for limiting aluminium contamination while providing enough calcium and phosphorus to meet the needs of patients, such as, for example, pediatric but also adult patients. This would also eliminate the need for precipitation curves in the pharmacies that take care of the compounding of the nutritional formulations.

However, it was found by Hall et al, Journal of Parenteral and Enteral Nutrition (2017), 41(7):1228-1233, that aluminium contamination in infant PN remains almost 3 times higher than the advised maximum exposure (<5 mcg/kg/d, FDA 2004). Accordingly, providing medical products for infusion, specifically pharmaceutical compositions for injection which can be used for preparing parenteral nutrition products comprising calcium and phosphate essentially without precipitation of calcium phosphate and, at the same time, with very low amounts of aluminium are urgently required.

The present invention addresses the need to further reduce the issues of aluminium toxicity while maintaining a low risk approach for precipitation. The drug substance or API (active pharmaceutical ingredient) sodium glycerophosphate available today, due to raw materials used and available processes for producing it also comprises certain amounts of aluminium, even though amounts are lower than in inorganic phosphate sources. Bringing down the amount of aluminium contained in sodium glycerophosphate as used for the preparation of pharmaceutical compositions or medical products for use in clinical nutrition or for infusion would render such medical products highly beneficial especially for use with pediatric patients, and specifically for the most vulnerable ones, pre-term babies and neonates. It would actually allow to increase the concentration of phosphate and calcium in the final parenteral nutrition formulations without running the risk of precipitation and, at the same time, again exceeding the recommended threshold for aluminium of 5 mcg/kg/d. SGP is stable in solutions compounded at concentrations up to 120 mmol/L and 96 mEq/L of calcium chloride, for example.

In the state of the art, micronutrients such as sodium phosphate, potassium phosphate or sodium glycerophosphate are typically added to nutrition bags before administration to the patient or are provided for compounding a parenteral nutrition formulation, such as with automatic compounding devices as described above. The compounds can also be added to IV solutions such as sodium chloride 0.9% w/v and glucose 5% w/v solutions for infusion. They are generally not for direct intravenous administration but are concentrated solutions for compounding or dilution in a PN formulation or solution for infusion. The currently available phosphate compositions are available in concentrations of from about 1 mmol/mL to about 3 mmol/mL of phosphate. The phosphate solutions are provided in glass vials, polypropylene ampoules, polyethylene vials or in non-PVC flexible bags.

Generally, medical products for injection and use in clinical nutrition should be prepared with a drug substance or API of highest purity. In case of SGP, it is a goal of the present invention to achieve high purity in terms of a very low amount of free phosphate, low amounts of aluminium and low amounts of so-called SGP related products. For the avoidance of doubt, the expressions "API" and "drug substance" are interchangeably used herein.

The drug substance and the medical product manufactured therefrom are intended to have a low content of free phosphate, as the free phosphate could result in the aforementioned unwanted precipitation with calcium and formation of calcium phosphate during and/or after compounding, especially when using the intended SGP in combination with inorganic calcium salts. SGP as drug substance for use in the preparation of a medical product and, accordingly, the resulting medical product should therefore contain as low amounts of free phosphate as possible.

In addition, it is desirable to reduce the amount of SGP related products which are generated during the production or synthesis of SGP. For a medical product, the presence of any by-products is undesirable, even it can be assumed that they are non-toxic and, therefore, no impurities as such. Accordingly, it is an object of the present invention to provide a SGP drug product and a medical product prepared therefrom which is characterized by a lower amount of SGP-related products compared to currently known and available drug products and medical products.

SGP compositions for infusion, including their use in clinical nutrition, are available on the European market, such as, for example, Glycophos® Sodium Glycerophosphate (Fresenius Kabi), which comprises 1 mmol of glycerophosphate and 2 mmol of sodium per mL, i.e., 1 mMol of phosphate per 1 mL. It is provided in 20 ml single dose plastic vials. In the United States, no pharmaceutical compositions comprising SGP as an organic phosphate source especially for compounding parenteral nutrition formulations are approved to date, even though Glycophos® received temporary authorization to be imported and distributed due to the critical shortage of phosphate injection in the U.S. market. The aluminum content of Glycophos® disclosed is "not more than 550 mcg/L (550 ppb)".

Methods for producing aqueous solutions of sodium glycerophosphate are known in the art and have been described, for example, in RU1667364C, wherein glycerol was reacted with a mixture of phosphoric acid and sodium dihydrogen phosphate at a molar ratio of 1:0.5-3 by heating under vacuum to a temperature of 140-150° C. and subsequent dilution of the reaction mixture with water and saponification with sodium hydroxide. In this way, yields of 86% could be achieved.

CN101851252B describes how SGP was prepared from sodium carbonate, phosphoric acid and glycerine, wherein the phosphoric acid and the glycerine were submitted to an esterification reactor, sodium carbonate was added vapor introduced; the pH value was from 3.0-5.5 in the reaction process and the reaction temperature was 120-145° C. The reaction was followed again by adding water and esterification by adding sodium hydroxide. After carrying out reflux for 8-12 hours and the addition of NaOH at a pH of 8.0-11.0, MgO was added according to the content of intermediate free phosphate after hydrolyzation so as to eliminate free phosphate generated in the reaction. The raw sodium glycerophosphate was concentrated and free glycerine was removed. The sodium glycerophosphate prepared by the method was reported to have a high content of beta-sodium glycerophosphate.

CN1517093A discloses a sodium glycerylphosphate solution for injection which was prepared from anhydrous sodium glycerylphosphate, hydrochloric acid and water for injection wherein the concentrated hydrochloric acid was added to the water for injection at 20-30° C. and dissolving the anhydrous sodium glycerylphosphate in it while stirring, followed by the addition of hydrochloric acid to regulate pH to 7.2-7.6. The solution was mixed with an amino acid or glucose solution before injection.

U.S. Pat. No. 4,576,930A describes a transfusion preparation containing glucose and electrolytes for intravenous infusion, the improvement comprising the preparation containing a salt of citric acid, salicylic acid, ethylenediaminetetraacetic acid or lactic acid as a chelating agent, and a pharmaceutically acceptable, water-soluble glycerophosphate such as, for example, sodium glycerophosphate, glucose-1-phosphate or glucose-6-phosphate as a phosphorous source, and having a pH of 5 to 7.5.

In light of what has been described before, there remains a need to develop methods for producing a sodium glycerophosphate drug substance as well as medical products comprising SGP for injection and use in clinical nutrition, wherein the drug substance and the medical product are characterized by a low aluminum content, low free phosphate content, and low amounts of SGP-related products.

SUMMARY OF THE INVENTION

In light of the prior art and the described challenges for safely and effectively providing phosphate and calcium to highly susceptible patients, the technical problem underlying the present invention is to provide a medical product comprising sodium glycerophosphate for injection and use in clinical nutrition in a concentration of from about 0.5 mmol/mL to about 30.0 mmol/mL, wherein the medical product is characterized by low amounts of aluminum, such as not more than about 500 ppb, preferably not more than about 400 ppb and especially preferably not more than about 300 ppb, a low amount of free phosphate and low amounts of SGP-related products.

This problem is solved by the features of the independent claims. Preferred embodiments of the present invention are provided by the dependent claims. The invention therefore relates to a medical product for injection comprising sodium glycerophosphate (SGP) in a concentration of from about 0.5 mmol/mL to about 30.0 mmol/mL, wherein the medical is characterized by amounts of aluminum not exceeding about 500 ppb. According to another embodiment of the invention the medical product is characterized by low amounts of free phosphate, preferably below about 5% of the total phosphate. According to yet another embodiment of the invention, the medical product is characterized by an amount of SGP-related substances of not more than about 15% (w/w) of the total phosphate.

According to one embodiment, the medical product according to the invention is provided in a concentration of from about 0.8 mmol/L to about 2.0 mmol/L.

According to another embodiment of the invention, the amount of free phosphate in the medical product is not more than about 3% (w/w) of the total phosphate, preferably not more than about 1% (w/w) of the total phosphate, more preferably not more than about 0.5% (w/w), and especially preferably not more than about 0.1% (w/w) of the total phosphate in the medical product.

According to another embodiment of the invention, the amount of SGP related substances in the medical product not more than about 15% (w/w) of the total phosphate, preferably not more than about 12% (w/w) of the total phosphate, and especially preferably not more than about 10% of the total phosphate. According to a specific embodiment of the invention, the SGP related substances are selected from the group of SGP related substances consisting of GlyceroDiPhosphate (GDP), DiGlyceroPhosphate (DGP), TriGlyceroPhosphate (TGP), DiGlyceroDiPhosphate (DGDP), TriGlyceroDiPhosphate (TGDP), Cyclic GlyceroDiPhosphate (CGDP and DiGlyceroTriPhosphate (DGTP).

According to another embodiment of the invention, the amount of aluminum in the medical product is not more than about 400 ppb, preferably not more than about 300 ppb, and especially preferably not more than about 250 ppb.

According to another embodiment of the invention, the ratio of alpha sodium glycerophosphate (α-SGP) and beta sodium glycerophosphate (β-SGP) in the medical product is from about 1:5 to about 5:1, preferably from about 1:2 to about 2:1, and especially preferably from about 1.5:1 to about 1:1.5, such as, for example, from about 1.2:1 to about 1:1.2.

According to another embodiment of the invention, the pH of the medical product is between about 6.0 to about 8.0, preferably from about 6.8 to about 7.8, such as for example, from about 7.0 to about 7.5 or from about 7.1 to about 7.7.

According to another embodiment of the invention, the medical product is terminally heat-sterilized. According to yet another embodiment of the invention, the medical product is sterile.

According to another embodiment of the invention, the medical product is provided in a concentration of SGP of from about 0.5 mmol/L to about 10 mmol/L, from about 0.5 mmol/L to about 5 mmol/L, or from about 0.8 mmol/L to about 2.0 mmol/L in polymeric container, such as a polymeric vial or flexible bag, having a volume of from about 50 mL to about 500 mL, preferably a volume of from about 80 mL to about 300 mL, such as about 100 mL or about 250 mL.

According to another embodiment of the invention, the medical product is stable at a temperature of from about 1° C. to about 25° C. for at least 12 months, preferably at least 18 months, and more preferably for at least 24 months.

According to another embodiment of the invention, the medical product is provided for intravenous administration after addition to or dilution in a solution for intravenous injection or infusion, such as a saline solution for intravenous injection or a parenteral nutrition product. According to one aspect of the present invention, the medical product is administration to a patient receiving parenteral nutrition. Specifically, the medical product is provided for administering phosphate to said patient, wherein the patient is an adult patient or a pediatric patient. According to yet another embodiment of the invention, the medical product is provided for preventing and/or treating phosphate deficiency, specifically in a patient receiving parenteral nutrition.

A "saline solution for intravenous injection or infusion" as used herein refers to solutions which are suitable for intravenous injection, including solutions comprising sodium chloride, such as, for example sodium chloride about 0.9% (w/v), glucose solutions, such as, for example, glucose about 5% (w/v) in water, Lactated Ringer's solution (also called Ringer's Lactate or sodium lactate solution), multiple electrolyte solutions such as, for example, Plasma-Lyte 148 (Baxter), an isotonic solution of electrolytes, or combinations thereof, such as, for example, sodium chloride about 0.9% w/v and glucose about 5% w/v solution for infusion (Baxter).

According to another embodiment of the invention, the medical product is for use in the compounding of parenteral nutrition formulations.

According to another embodiment of the invention, is used for supplementation of ready-to-use parenteral nutrition products.

According to another embodiment of the invention, the medical product is provided for administering phosphate to a patient, specifically to a patient who receives parenteral nutrition. According to another embodiment, the medical product serves for the prevention and/or treatment of phosphate deficiency of a patient. A patient in the context of the present invention can be an adult or a pediatric patient.

According to yet another aspect of the invention, the medical product is prepared from the API (SGP) by dissolving the SGP in water for injection under close pH control, wherein the pH is adjusted to a pH in the range of from about 6.0 to about 8.0, preferably to a pH of from about 6.8 to about 7.8, such as for example, from about 7.0 to about 7.5 or from about 7.1 to about 7.7. The pH is adjusted preferably with hydrochloric acid. The pH adjusted SGP solution is then filled into flexible bags of the desired size, the bags are sealed and overpouched and submitted to sterilization, preferably terminal heat-sterilization. According to yet another embodiment, the SGP used for preparing the medical product comprises not more than about 500 pbb, not more than about 400 ppb, not more than about 300 ppb and not more than about 250 ppb of aluminum, not more than about 15% (w/w), not more than about 12% (w/w) or not more than about 10% (w/w) of SGP related substances and not more than about 5%, not more than about 3% (w/w), not more than about 1% (w/w), not more than about 0.5% (w/w) or not more than about 0.1% (w/w) of free phosphate.

All features disclosed in the context of the medical product according to the invention also relate to the method of preparing such a medical product and are herewith disclosed also in the context of the method of preparing the medical product. The same holds true for SGP as an API, methods of preparing same and for preparing a medical product according to the invention from such API.

BRIEF DESCRIPTION OF DRAWINGS

The invention is further described by the following figures. These are not intended to limit the scope of the invention but represent preferred embodiments of aspects of the invention provided for greater illustration of the invention described herein.

DETAILED DESCRIPTION OF THE INVENTION

Figure 1:
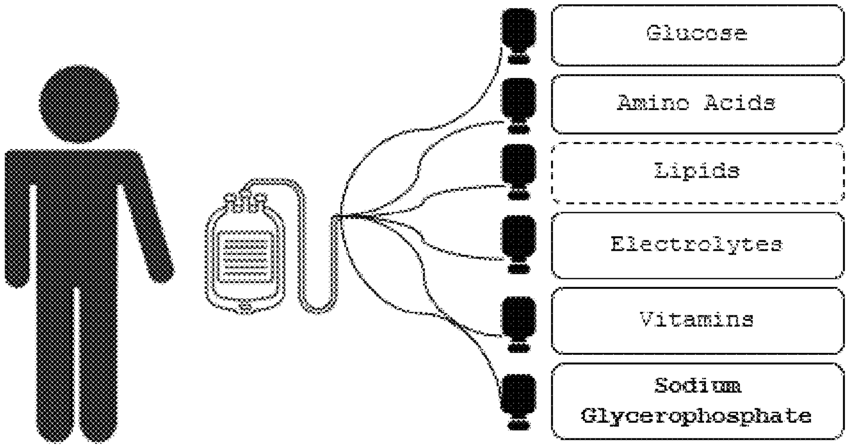
FIG. 1 is a schematic representation of the compounding of a parenteral nutrition formulation for injection.

All cited documents of the patent and non-patent literature are hereby incorporated by reference in their entirety.

Definitions

Some definitions are provided hereafter. Nevertheless, definitions may be located in the "Embodiments" section below, and the above header "Definitions" does not mean that such disclosures in the "Embodiments" section are not definitions.

All percentages expressed herein are by weight of the total weight of the composition unless expressed otherwise. As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number. All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a component" or "the component" includes two or more components.

The words "comprise," "comprises" and "comprising" are to be interpreted inclusively rather than exclusively. Likewise, the terms "include," "including" and "or" should all be construed to be inclusive, unless such a construction is clearly prohibited from the context. Nevertheless, the compositions disclosed herein may lack any element that is not specifically disclosed herein. Thus, a disclosure of an embodiment using the term "comprising" includes a disclosure of embodiments "consisting essentially of" and "consisting of" the components identified.

The term "and/or" used in the context of "X and/or Y" should be interpreted as "X," or "Y," or "X and Y." Similarly, "at least one of X or Y" should be interpreted as "X," or "Y," or "X and Y." For example, "at least one dithionite or a functionally similar reducing agent" should be interpreted as "dithionite," or "a functionally similar reducing agent," or "both dithionite and a functionally similar reducing agent."

Where used herein, the terms "example" and "such as," particularly when followed by a listing of terms, are merely exemplary and illustrative and should not be deemed to be exclusive or comprehensive. As used herein, a condition "associated with" or "linked with" another condition means the conditions occur concurrently, preferably means that the conditions are caused by the same underlying condition, and most preferably means that one of the identified conditions is caused by the other identified condition.

Embodiments

The present invention is directed to a stable, sterilized medical product comprising sodium glycerophosphate (SGP) in a concentration of from about 0.5 mmol/mL to about 5.0 mmol/mL, wherein the amount of free phosphate is below about 5% (w/w) of the total phosphate, the amount of SGP related substances is below about 15% (w/w) of the total phosphate, and the amount of aluminum is below about 300 ppb. Preferably, the ratio of alpha sodium glycerophosphate (α-SGP) and beta sodium glycerophosphate (β-SGP) in the medical product is from about 1:1.5 to about 1.5:1.

It was the goal of the invention to provide such medical product for use in providing phosphate to patients via parenteral nutrition, wherein the medical product is of high purity regarding by-products (SGP-related products), has a very low amount of aluminum and, at the same time, a very low amount of free phosphate. So far, no product fulfilling all these requirements has been described or provided, while it is urgently needed especially for very vulnerable patients such as newborns requiring parenteral nutrition and who need increased amounts of phosphate while being very susceptible to aluminum contamination.

The expression "medical product(s)" is interchangeably used herein with the expressions "pharmaceutical product(s)" and "pharmaceutical composition(s)". Such "medical product" relates to any product designed for and intended to be used for medical purposes, preferably for injection. Specifically, a "medical product" according to the invention is designed for and can be used for the preparation of compounded parenteral nutrition products and for injection in products intended for parenteral nutrition, and is preferably designed for use in the compounding of parenteral nutrition formulations for injection and/or for being added to a pre-prepared, ready-to-use parenteral nutrition formulation or parenteral nutrition product before administration to a patient.

The term "stable" as used herein in connection with SGP means that at least 80%, at least 90%, at least 95%, at least 98% or at least 99% of the amount of SGP initially provided in the product is still available after terminal heat-sterilization and storage of the terminally heat-sterilized product of the invention for at least 12 months, for at least 18 months and preferably for at least 24 months at a temperature of from 1° C. to 25° C. and/or for at least 6 months and preferably for at least 8 months at temperatures of from 1° C. to 40° C. Generally, it will be assumed that the amount of SGP "provided in the product" corresponds to the amount of SGP in the product immediately after terminal heat sterilization. Accordingly, it is one embodiment of the invention that the medical product is stable at a temperature of from 1° C. to 25° C. for at least 12 months, preferably at least 18 months, and more preferably for at least 24 months.

As used herein, the term "adult" refers to persons of 20 years of age and older. The term "pediatric" refers to neonates, including premature (pre-term), full term, and post-mature neonates of up to one month of age; infants of between one month and one year of age; children of between one and up to 12 years of age, and adolescents of between 13 and up to 19 years of age.

The expression "free phosphate" as used herein refers to the phosphate anion $[PO_4]^{3-}$, hydrogen phosphate $[HPO_4]^{2-}$, dihydrogen phosphate $[H_2PO_4]^-$, or phosphoric acid $H_3PO_4$, depending on the pH, and encompasses the respective salts thereof. At physiological (homeostatic) pH, free phosphate primarily consists of a mixture of $[HPO_4]^{2-}$ and $[H_2PO_4]^-$ ions. It was one of the goals of the present invention to reduce the presence, amount and generation of free phosphate in the SGP drug product and the medical product prepared therefrom by optimizing the production of both the SGP drug product, i.e. the chemical synthesis, and the preparation process of the final medical product. The major goal and benefit of reducing the amount of free phosphate is to further reduce the risk of precipitation of calcium phosphate which may potentially not be detectable by visual inspection and may occur during compounding, during mixing with a pre-prepared or ready-to-use parenteral nutrition product, and/or during administration to the patient.

The expression "sodium glycerophosphate" or "SGP" refers to the sodium salt form of an organic phosphate compound that provides phosphate for nutritional purposes (Table I). The active pharmaceutical or drug substance SGP is hydrated. SGP is freely soluble in water and essentially insoluble in acetone and in ethanol. SGP is hygroscopic. For the avoidance of doubt, the expression "SGP", if not expressly stated otherwise, does not encompass any SGP related products. SGP is described in Ph. Eur. (monograph n° 1995). SGP occurs as alpha-SGP and as beta-SGP, see again Table I. When using the expression SGP, both alpha-SGP and beta-SGP are encompassed if not expressly stated otherwise.

SGP is also known, for example, as (2RS)-2,3-dihydrooxypropyl phosphate, sodium 2-hydroxy-1-(hydroxymethyl)ethyl phosphate, glycerolmonophosphoric acid ester sodium salt, 1,2,3-propanetriol mono(dihydrogen phosphate) disodium salt, or disodium glycerol phosphate. Sodium glycerophosphate is one of several glycerophosphate salts. It is used clinically to treat or prevent low phosphate levels. Glycerophosphate is hydrolysed to inorganic phosphate and glycerol in the body. The extent of this reaction is dependent on the activity of serum alkaline phosphatases. Maximum hydrolysis occurs at a plasma concentration of >0.7 mmol/L. Where hydrolysis of glycerophosphate completely occurs in plasma, about 12-15 mmol of sodium glycerophosphate are hydrolyzed each day in individuals with normal serum alkaline phosphatase.

According to one embodiment of the invention, a medical product or pharmaceutical composition is provided provide which comprises sodium glycerophosphate for injection and use in clinical nutrition in a concentration of from about 0.5 mmol/mL to about 5.0 mmol/mL. According to another embodiment of the invention, the medical product comprises from about 0.8 mmol/L to about 3.5 mmol/L. According to another embodiment of the invention, the medical product comprises from about 0.8 mmol/L to about 2.0 mmol/L. According to yet another embodiment of the invention, the medical product comprises from about 1.0 mmol/L to about 1.5 mmol/L.

According to one embodiment of the invention the medical product for injection comprises sodium glycerophosphate (SGP) in a concentration of from about 0.5 mmol/mL to about 5.0 mmol/mL, wherein the medical product is characterized by low amounts of aluminum, preferably below about 300 ppb. According to another embodiment of the invention, the medical product is further characterized by low amounts of free phosphate, preferably below about 5% of the total phosphate. According to yet another embodiment of the invention, the medical product is further characterized by a low amount of SGP-related substances, wherein the amount of SGP-related products in the medical product is below about 15% (w/w) of the total phosphate.

According to another embodiment of the invention, the amount of free phosphate in the medical product is below about 3% (w/w) of the total phosphate, preferably below about 1% (w/w) of the total phosphate, more preferably below about 0.5% (w/w), and especially preferably below about 0.1% (w/w) of the total phosphate in the medical product.

The expression "SGP related product(s)" refers to esters of glycerol and phosphate which are generated during the production or synthesis of SGP. For avoidance of doubt, the expression "SGP related products" as used herein does not encompass alpha-SGP, beta-SGP, glycerol and phosphate (Alpha-GP, Beta-GP, Gly and Phos in Table I). Typical SGP related products are shown in Table I. Further esters of glycerol and phosphate can be formed but they are present at lower amounts and are not shown in the table. For a medical product, the presence of any such SGP-related products is generally undesirable, even though it can be assumed that they can also serve as phosphate sources and are non-toxic and, therefore, are no classical impurities. Accordingly, it was an object of the present invention to provide an SGP drug product or API and a medical product prepared therefrom which is characterized by the absence and/or a low amount of SGP-related products. This could be achieved by a new and optimized process of preparing the SGP drug product and the final medical product. In the context of the present invention, special reference is made to the group of SGP related substances consisting of glycerodiphosphate (GDP), diglycerophosphate (DGP), triglycerophosphate (TGP), diglycerodiphosphate (DGDP), triglycerodiphosphate (TGDP), and diglycerotriphosphate (DGTP) as shown in Table I. CGDP is not shown.

TABLE 1 the group of SGP related substances.

| Abbr. | Name | Empirical Formula | Structure (only one isomer is shown) |
|---|---|---|---|
| Gly | Glycerol | $C_3H_8O_3$ | 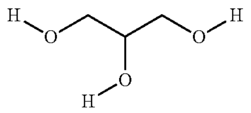 |
| Phos | Phosphate | $PO_4$ | 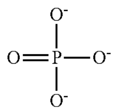 |
| Alpha-GP (α-SGP) | α-Glycero-phosphate | $C_3H_7O_6P$ | 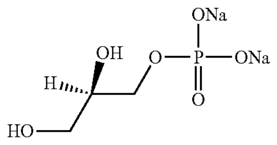 |
| Beta-GP (β-SGP) | β-Glycero-phosphate | $C_3H_7O_6P$ | 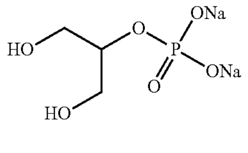 |

TABLE 1-continued
the group of SGP related substances.
| Abbr. | Name | Empirical Formula | Structure (only one isomer is shown) |
|---|---|---|---|
| GDP | Glycero-diphosphate | $C_3H_6O_9P_2$ | 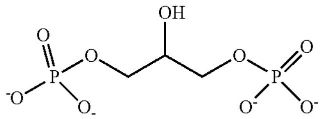 |
| DGP | Diglycero-phosphate | $C_6H_{10}O_8P$ | 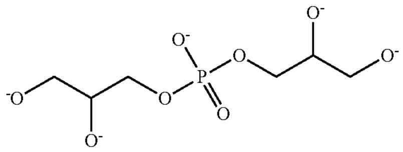 |
| TGP | Triglycero-phosphate | $C_9H_{15}O_{10}P$ | 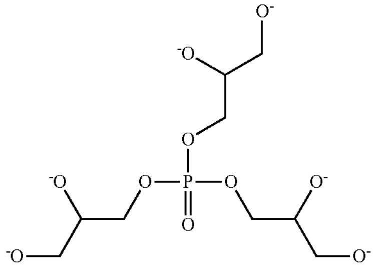 |
| DGDP | Diglycero-diphosphate | $C_6H_{10}O_{11}P_2$ | 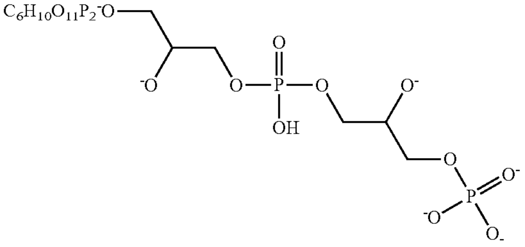 |
| TGDP | Triglycero-diphosphate | $C_9H_{15}O_{13}P_2$ | 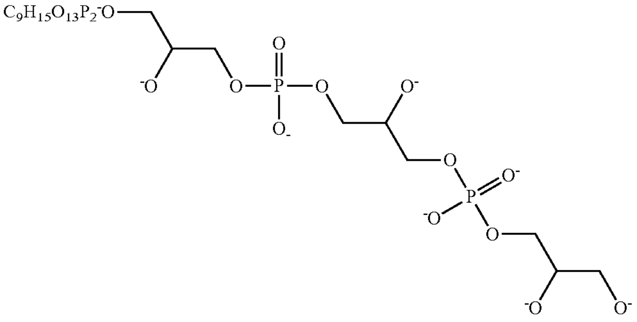 |
| DGTP | Diglycero-triphosphate | $C_6H_{10}O_{14}P_3$ | 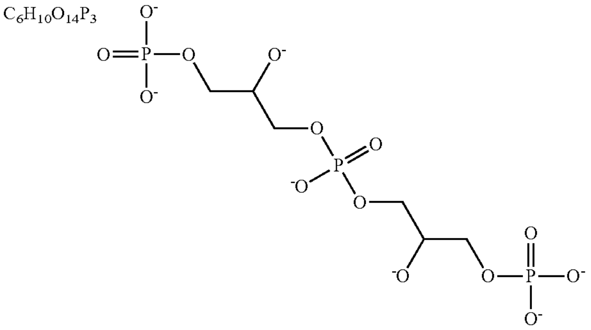 |

According to one embodiment of the invention, the amount of SGP-related substances in the medical product is below about 15% (w/w) of the total phosphate, preferably below about 12% (w/w) of the total phosphate, and especially preferably below about 10% of the total phosphate. According to a specific embodiment of the invention, the SGP related substances are selected from the group of SGP related substances consisting of glycerodiphosphate (GDP), diglycerophosphate (DGP), triglycerophosphate (TGP), diglycerodiphosphate (DGDP), triglycerodiphosphate (TGDP), and diglycerotriphosphate (DGTP) and cyclic glycerodiphosphate (CGDP).

SGP and SGP-related products (amount of total and individual compounds) can be determined in a given drug substance or medical product via chromatographic separation (HPLC or UPLC) followed by CAD, Charged Aerosol Detection (Corona®). This method can also be used to determine the amount of alpha- and beta-SGP and any impurities and is therefore a feasible option to determine the quality of a new chemical synthesis method to produce a SGP drug substance according to the invention, so an improved medical product with a low content of SGP-related substances can be provided. Other methods can also be used, such as, for example, NMR or LC-MS methods.

It was another aim of the present invention to provide an SGP drug product and a medical product prepared therefrom which has a significantly lower aluminum content in comparison to the known prior art. Preferably, the aluminum concentration is below about 300 ppb, below about 275 ppb, below about 250 ppb and especially preferably below about 225 ppb, in order to obtain a medical product that can be used for the preparation of parenteral nutrition formulations for the safe administration to patients, including pediatric patients.

The aluminum concentration can be determined as described, for example, in Example 3. Basically, the aluminum determination analysis can be performed by Inductively Coupled Plasma Mass Spectrometry (ICP-MS). Inductively Coupled Plasma Mass Spectrometry (ICP-MS) is a type of mass spectrometry that is highly sensitive and capable of the determination of a wide range of metals at trace levels (one part per billion (ppb) level). It is based on the combination of an inductively coupled plasma as a method of producing ions with a mass spectrometer as a method of separating and detecting the ions.

According to another embodiment of the invention, the ratio of alpha sodium glycerophosphate ($\alpha$-SGP) and beta sodium glycerophosphate ($\beta$-SGP) in the medical product is from about 1:2 to about 2:1, preferably from about 1.5:1 to about 1:1.5, and especially preferably from about 1.2:1 to about 1:1.2.

According to yet another embodiment of the invention, the pH of the medical product is between about 5.0 to about 8.0, preferably from about 6.0 to about 7.5.

Figure 3:
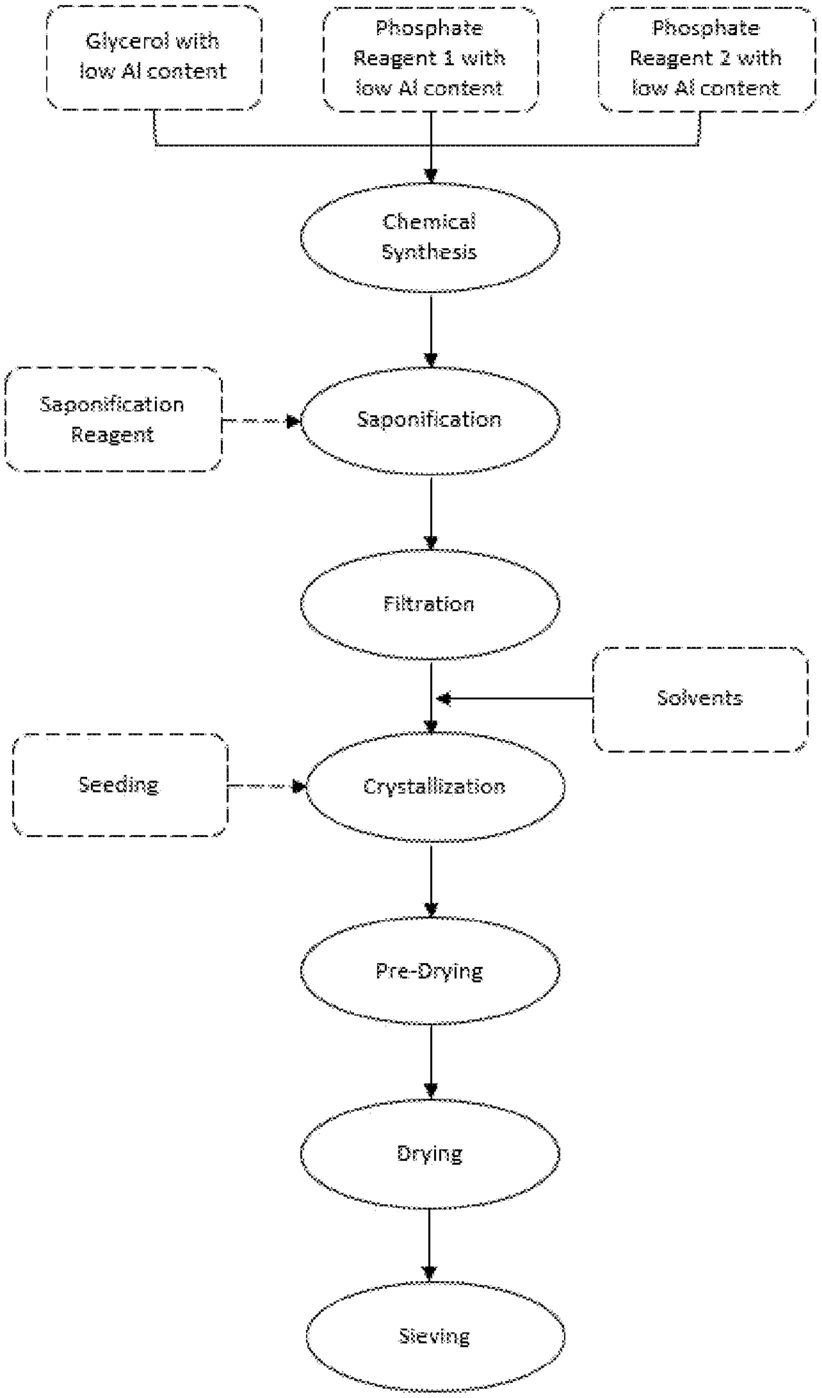
FIG. 3 is a schematic representation of the process to produce an SGP pharmaceutical drug product for use in the production of a medical product according to the invention.
Figure 4:
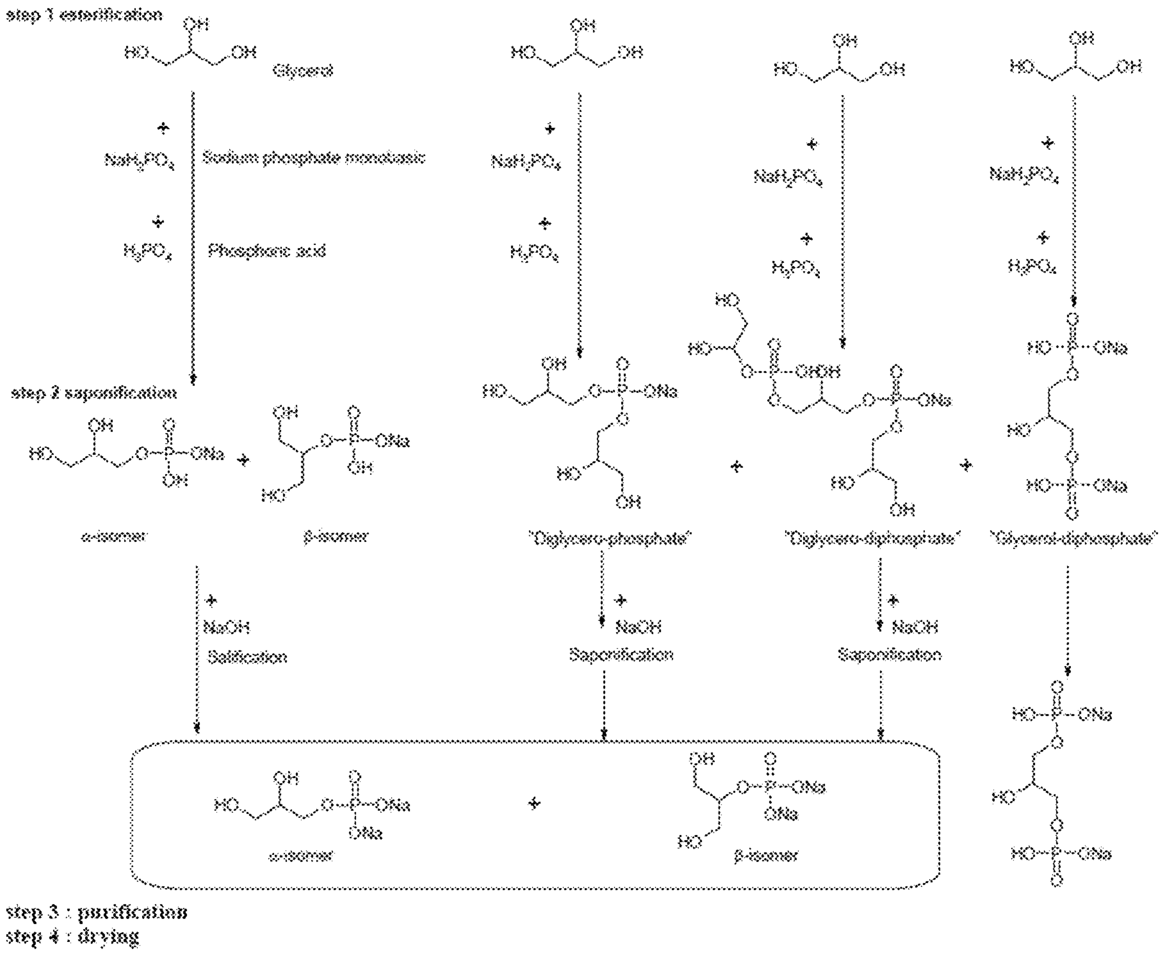
FIG. 4 shows a reaction scheme for the synthesis of SGP. The esterification step is followed by saponification. Purification and drying are not shown in detail. SGP is produced as α- and β-isomer. See also Example 1.

According to another embodiment of the invention, a process for producing an SGP drug product for use in the production of a medical product according to the invention is disclosed. The process is schematically depicted in FIGS. 3 and 4. Phosphate based reactions are known to be very complex and may lead to non-reproducible results. Various intermediates may occur as shown, for example, in FIG. 4, and the content of free phosphate and SGP-related products may vary. Also, the ratio between alpha- and beta-SGP can be influenced. As a first step, the starting materials glycerol, phosphoric acid and sodium phosphate should be carefully selected, and their impurity profile should be monitored throughout the manufacturing process regarding Al content, including analyzing individual lots and selecting only such raw materials and lots that fulfil the required standard. Importantly, neither catalysts nor other reagents or protecting agents are required in the process according to the invention to obtain the SGP product which could be another source of potential impurities, including aluminum or other inorganic or elemental impurities. In order to further control the introduction of aluminum, the starting materials glycerol, phosphoric acid and sodium phosphate should be tested and selected in a way that they have an aluminum content below the level of quantification. In addition, care must be taken to avoid reactors, vessels or sieves that could introduce elemental impurities such as, for example, Cr, Ni, Mo, Ti or Mn. Rather, stainless steel equipment should be used throughout to avoid any such contamination. As a result, the level of metallic residues is consistently low in the SGP drug product and resulting pharmaceutical composition according to the invention. As shown in Table II, analytical results of ICS-MS on elemental impurities confirm that the concentration of Cd, PB, AS, Hg, CO, V, Ni, Tl, Au, Pd, Ir, Os, Rh, Ru, Se, Ag, Pt, Li, Sb and Cu are below 0.10 ppm in the batches tested, and therefore well below concentration limits (ppm) provided for by the ICH guideline Q3D (R1) on elemental impurities (Mar. 28, 2019). Also, Ba, Mo, Sn and Cr are significantly lower than the guidelines requests. The content of barium (Ba) is generally below 1.0 ppm, preferably below 1.5 ppm, and especially preferably below 1.0 ppm in the SGP drug product and medical product according to the invention. The content of molybdenum (Mo) is generally below 2.0 ppm, preferably below 0.75 ppm, and especially preferably below 0.5 ppm in the SGP drug product and medical product according to the invention. The content of tin (Sn) is generally below 0.8 ppm, preferably below 0.5 ppm, and especially preferably below 0.2 ppm in the SGP drug product and medical product according to the invention. The content of chromium (Cr) is generally below 1.0 ppm, preferably below 0.3 ppm, and especially preferably below 0.2 ppm in the SGP drug product and medical product according to the invention.

TABLE II

Analytical results of ICP-MS on elemental impurities. Results for on exemplary batch are shown and can be compared directly with the limit provided for by ICH guideline Q3D (R1) on elemental impurities.

| Name | | ICH Concentration Limit (ppm) | Batch no 25002575/C level (ppm) |
|---|---|---|---|
| Cadmium | Cd | 0.2 | <0.10 |
| Lead | Pb | 0.5 | <0.10 |
| Arsenic | As | 1.5 | <0.10 |
| Mercury | Hg | 0.3 | <0.10 |
| Cobalt | Co | 0.5 | <0.10 |
| Vanadium | V | 1 | <0.10 |
| Nickel | Ni | 2 | <0.10 |
| Thallium | Tl | 0.8 | <0.10 |
| Gold | Au | 10 | <0.10 |
| Palladium | Pd | 1 | <0.10 |
| Iridium | Ir | 1 | <0.10 |
| Osmium | Os | 1 | <0.10 |
| Rhodium | Rh | 1 | <0.10 |
| Ruthenium | Ru | 1 | <0.10 |
| Selenium | Se | 8 | <0.10 |
| Silver | Ag | 1 | <0.10 |
| Platinum | Pt | 1 | <0.10 |
| Lithium | Li | 25 | <0.10 |
| Antimony | Sb | 9 | <0.10 |
| Barium | Ba | 70 | 1.00 |
| Molybdenum | Mo | 150 | 0.25 |
| Copper | Cu | 30 | <0.10 |

TABLE II-continued

Analytical results of ICP-MS on elemental impurities. Results for on exemplary batch are shown and can be compared directly with the limit provided for by ICH guideline Q3D (R1) on elemental impurities.

| Name | | ICH Concentration Limit (ppm) | Batch no 25002575/C level (ppm) |
|---|---|---|---|
| Tin | Sn | 60 | 0.18 |
| Chromium | Cr | 110 | 0.09 |

Regarding intermediate products, every intermediate product can be considered as a potential impurity. These products mostly are diglycero-phosphate (DGP) isomers; diglycero-diphosphate (DGDP) isomers; glycerol-diphosphate (GDP) isomers. Diglycerophosphate, diglycero-diphosphate and glycerol-diphosphate, which are SGP-related products, may be formed, for example, during esterification. The formation of these SGP-related products is controlled to a significant extent by the reaction time which in turn is controlled by the kinetics of the esterification reaction. Longer reaction times showed to increase the level of SGP-related substances. The parameters, in order of magnitude, impacting the most the kinetic, are the reaction temperature, the pressure applied and the pH (quantity of acid). The reaction time in no case should be exceeding 73 h. Regarding the formation of phosphoric acid, degradation studies showed that the amount of phosphoric acid increases when heat reaches 80° C. So, temperature and reaction time must be managed carefully throughout the process to avoid the generation of phosphoric acid as a degradation product and must be balanced again the generation of SGP-related products during the esterification step.

According to one embodiment of the invention, the process for producing SGP comprises the steps of (a) Reacting a mixture of phosphoric acid and sodium phosphate, preferably at a ratio of about 20:80, with glycerol at a temperature of from about 130° C. to about 150° C. to form a reaction mixture;

(b) Distilling off water which is generated during the reaction from the reaction mixture;

(c) Saponifying, preferably at a pH of between 12 and 13 and a pressure of from 20 mbar to 275 mbar, and maintaining the reaction mixture at about 90° C. to 110° C., preferably at about 100° C., for about 2 to 5 hours, preferably for about 3 hours;

(d) Crystallizing the sodium glycerophosphate by precipitation from a solution of the reaction mixture comprising the sodium glycerophosphate in water and ethanol; and optionally (e) Drying the sodium glycerophosphate.

According to one embodiment, the reaction of step (a) is done with monobasic sodium phosphate. Preferably, glycerol is added at about 3 to 6 eq, such as, for example, about 4 eq.

According to one embodiment, the saponification step is performed under stirring at about 220 rpm to about 500 rpm, such as from about 220 to about 300 rpm or from about 230 to about 270 rpm, such as, for example, at about 250 rpm.

According to one embodiment, saponification is done with sodium hydroxide, preferably with about 0.3 to about 0.4 equivalents. After saponification, the solution is preferably subjected to filtration in order to remove precipitated salts before crystallization. Glycerol is eliminated at the end of the process during crystallization in ethanol and successive washes. The monitoring of glycerol removal can be routinely performed on the final SGP drug substance. Glycerol impurities according to the invention are below the detection limit of 40.0 mg/kg.

According to one embodiment of the invention, saponification is done at a pressure of from about 100 mbar to about 270 mbar, about 150 mbar to about 270 mbar or about 230 mbar to about 270 mbar, such as, for example, at about 235 mbar, about 240 mbar, about 245 mbar, about 250 mbar, about 255 mbar, about 260 mbar or about 265 mbar. According to one embodiment, the pressure used is about 245 mbar, about 250 mbar or about 255 mbar.

According to one embodiment, the solution from which sodium glycerophosphate crystals are precipitated comprises from about 100 g/L to about 500 g/L of sodium glycerophosphate, preferably from about 200 g/L to about 300 g/L of SGP, such as, for example, about 200 g/L, about 210 g/L, about 220 g/L, about 230 g/L, about 240 g/L, about 250 g/L, about 260 g/L, about 270 g/L, about 280 g/L, about 290 g/L or about 300 g/L.

According to another embodiment, crystallization is performed at a temperature of from about 1° C. to about 20° C., preferably at a temperature of from about 5° C. to about 15° C., such as for example, at a temperature of about 6° C., about 7° C., about 8° C., about 9° C., about 10° C., about 11° C., about 12° C., about 13° C., about 14° C. or about 15° C.

According to one embodiment, crystallization is done in water to which ethanol is slowly added, for example over about 30 minutes to about 2.5 hours. Generally, adding ethanol over about 1 to about 2 hours will be enough. Preferably, the ethanol is added at a temperature of about 1° C. to about 20° C., preferably at a temperature of from about 5° C. to about 15° C., such as about 10° C., until a mixture water in ethanol of about 50% (v/v) to about 60% (v/v) is reached. The pH of the solution may vary over a relatively broad range and may be from about 8.0 to about 12.5.

According to one embodiment, the crystallization can then be supported by seeding (e.g. 0.25-0.33p), for example with SGP crystals consisting of alpha- and beta-SGP in a ratio of about 1:1. The solution should can be kept standing for about 1 to 8 hours, preferably for about 3 to about 7 hours, such as about 3, about 4, about 5, about 6, or about 7 hours, at a temperature of about 1° C. to about 20° C., preferably at a temperature of from about 5° C. to about 15° C., such as about 10° C.

According to a further embodiment, more ethanol can be added after the said holding time. Adding ethanol can be done over a time period of again over about 3 to about 8 hours, about 1 to about 8 hours, preferably for about 3 to about 7 hours, such as about 3, about 4, about 5, about 6, or about 7 hours, at a temperature of about 1° C. to about 20° C., preferably at a temperature of from about 5° C. to about 15° C., such as about 10° C., to achieve a about 15-40% (v/v) mixture of water in ethanol. Preferably, a mixture of water in ethanol of about 20%-35% (v/v) is achieved.

According to yet another embodiment, another seeding step is added as described before. After seeding (e.g., 0.25-0.33p), the solution should again be kept for several hours (e.g., between 3 and 8 hours, e.g., 5 hours) at the same temperature of about 5° C. to 15° C. as before (e.g., at 10° C.).

The formed crystals can then be filtrated and, where needed, the mother liquor can be used to push the product from the crystallization reactor. According to one embodiment, the SGP crystals are dried, for example in a stream of nitrogen for about 24 hours at about 20° C. (i.e. RT). Alternatively, drying can also be done by a stream of nitrogen under vacuum.

According to one embodiment of the invention, the SGP drug substance (hydrated) is packaged in a double low-density polyethylene bag (LDPE), and the double polyethylene bag is placed in a cardboard drum which is sealed, e.g., with metal clamps. The quality of the LDPE resin should comply with the European Pharmacopoeia monograph *PhEur.*3.1.3 *Polyolefin* with additive, or *PhEur.*3.1.4 *Polyethylene without additives* for containers, with external antistatic additive; Current European regulation on plastic materials and articles intended to come into contact with food, Commission Regulation (EU) No 10/2011 and related amendments.

Figure 5:
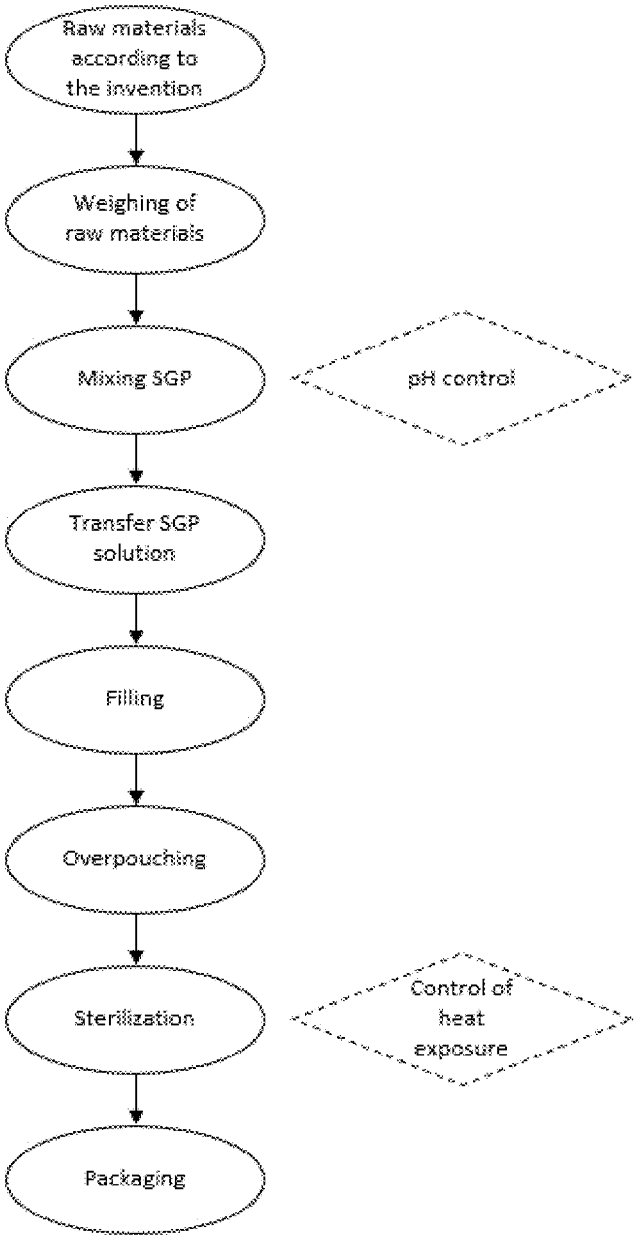
FIG. 5 provides for a schematic representation of the production of a pharmaceutical composition according to the invention, starting from the SGP raw material as produced according to what is shown in FIG. 4. Two of the most critical steps are indicated, i.e. pH control during mixing and control of heat exposure during sterilization.
Figure 6:
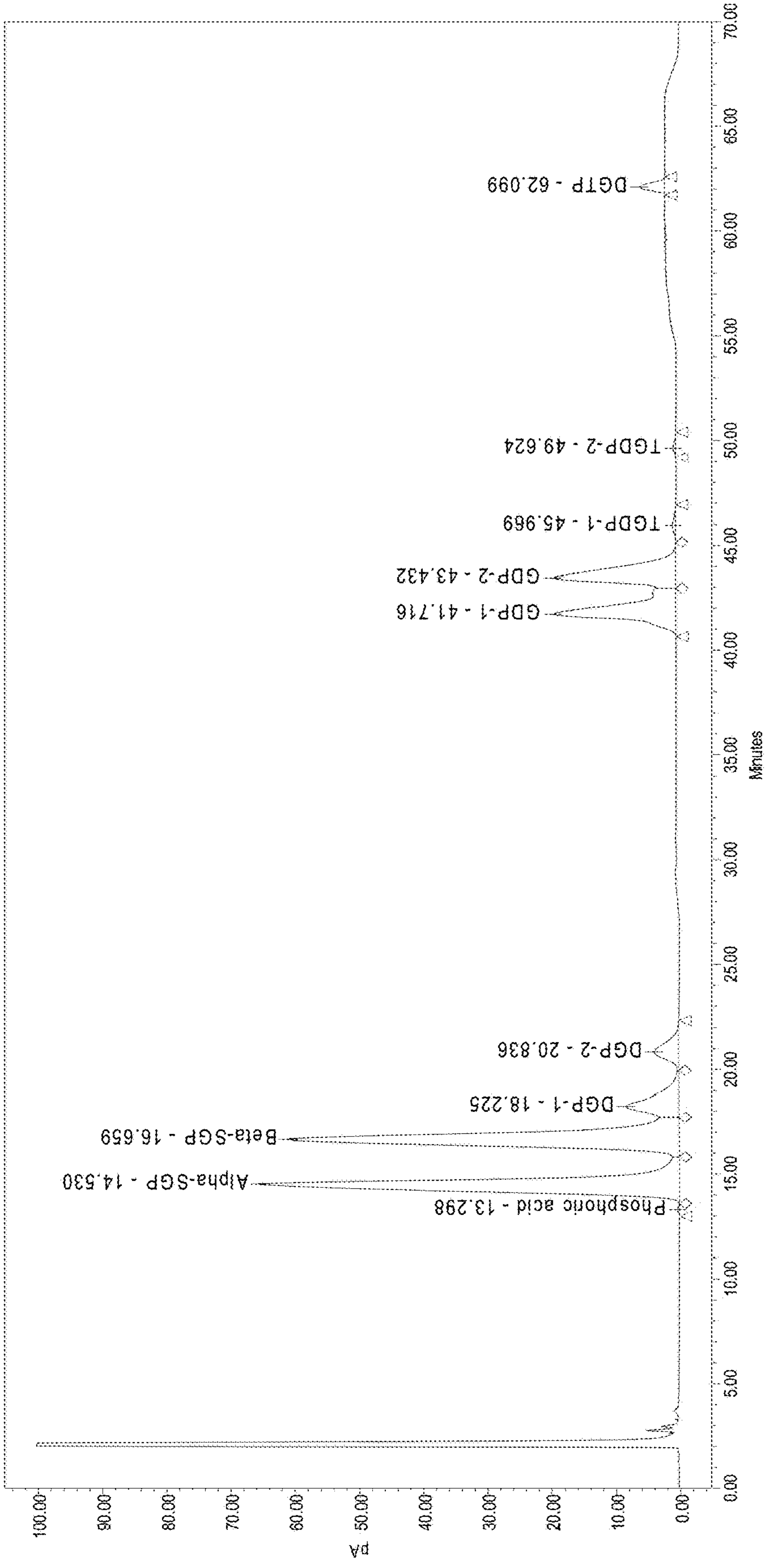
FIG. 6 shows an example of an SGP raw material sample chromatogram at 7.2 mg/mL. SGP-related products which could be identified are DGP, GDP, TGDP and DGP, see Table I. The chromatogram also identifies stereoisomers (e.g. GDP-1 and GDP-2) of the SGP-related products.

According to another embodiment of the invention, a process to produce a medical product according to the invention from a pharmaceutical drug substance (SGP) according to the invention is provided. It was found that critical steps in producing such finished medical product encompass, for example, the careful control of the pH and the careful control of the heat exposure during sterilization. A schematic representation of the production of the finished medical product is provided in FIG. 5.

According to one embodiment of the invention, the process for preparing the medical product comprises the steps of (a) Providing water for injection at a temperature of from about 30° C. to about 50° C., preferably at about 35° C. to about 45° C.;
(b) Adjusting the pH to about 7.2 to about 7.6;
(c) Dissolving SGP in the water for injection under pH control;
(d) Optionally cooling the solution to a temperature of not more than about 28° C., preferably about 25° C.;
(e) Filling of the SGP solution into a container and sealing the container;
(f) Overpouching the filled container;
(g) Sterilizing the medical product after step (c) or step (d) under control of heat exposure; and
(h) Optionally packaging the overpouched and sterilized container.

According to one embodiment of the invention, about 70% of the water for injection (WFI) needed for the final solution is provided before addition of SGP and is then added up to Q.S. after step (c).

According to another embodiment of the invention, the water for injection is heated to a temperature of about 40° C.

According to another embodiment of the invention, the pH is adjusted in step (b) with 25% HCl.

According to another embodiment of the invention, the solution is stirred for about 20 to about 40 minutes after step (c) and the adding up of the solution with WFI to Q.S.

According to yet another embodiment of the invention, the pH is adjusted to about 7.3 to about 7.6, such as about 7.4 or about 7.5, preferably to about 7.4, after step (C), preferably with 0.5% HCl.

In embodiments of the invention, the pharmaceutical composition is a sterilized solution. In the context of the invention, the term "sterilized" relates to a solution that has undergone a process of sterilization. Sterilization refers to any process that eliminates, removes, kills, or deactivates all forms of life (in particular referring to microorganisms such as fungi, bacteria, viruses, spores, unicellular eukaryotic organisms such as *Plasmodium*, etc.) and other biological agents like prions present in a specific surface, object or fluid, for example food or biological culture media. Sterilization can be achieved through various means, including heat, chemicals, irradiation, high pressure, and filtration. Sterilization is distinct from disinfection, sanitization, and pasteurization, in that those methods reduce rather than eliminate all forms of life and biological agents present. After sterilization, an object is referred to as being sterile or aseptic. The expression "terminally heat sterilized" or "terminal heat sterilization" as used herein refers to sterilization which takes place after the product has been filled into the primary packaging. Because of this, there are no further opportunities for contamination due to intervention. For example, terminal sterilization with moist heat (i.e., steam) is recommended by all pharmacopeias, for example with heating to 121° C. at 15 psi for 15 minutes.

According to one embodiment of the invention, sterilization is done by heat. As mentioned above, sterilization may involve heating under pressure in the presence of water to generate steam. Other methods encompass sterilization with moist heat. Sterilization by "moist heat" includes the use of saturated steam, steam air and hot water cascade or water spray sterilization. Sterilization with moist heat allows to reduce the total heat exposure of a solution to be sterilized. Sterilization can also be achieved via dry heating. Much higher temperatures (about 180-200° C.) are required for this method. Dry heating is commonly used to sterilize glassware, metal and other surfaces.

According to a specific embodiment of the invention, it is critical to tightly control the heat exposure of the bags during sterilization. Accordingly, sterilization is preferably performed by a multi-cycle sterilization process. Fo-values are used to determine the exposure time of a material for sterilization, in minutes, at a temperature of about 121° C. The Fo-values for sterilizing the medical product of the invention are selected, according to one embodiment, to a maximum Fo of about 40.0 minutes, a minimum Fo of about 6.1 minutes and a maximum delta of T (T=sterilization temperature in ° C.) of 2° C. The sterilization cycle/process used must be reproducible from load to load and from sterilizer to sterilizer to guarantee that a $10^{-6}$ Sterility Assurance Level (SAL) is provided for the medical product.

Exposure to radiation is another sterilization method used throughout the industry. Gamma radiation is the most common, though other options include infrared and ultraviolet radiation and high-velocity electrons. Radiation is typically used for the sterilization of single-use components/systems, but it can also be used for packaged drug products.

Treatment with gases is also a sterilization alternative. Such gases include ethylene oxide, formaldehyde, glutaraldehyde, propylene oxide, hydrogen peroxide and chlorine dioxide. This method is more commonly used to sterilize clean-room suites. Sterilization via filtration is the only option if the other processes are not suitable for the specific product or component. In filtration, the final drug product solution is passed through a filter that has been produced under aseptic manufacturing conditions and designed with appropriate pore sizes/surface chemistries that remove bacteria via size exclusion, entrapment, electrostatic attraction and other modalities.

In the context of the invention, the pharmaceutical composition is provided in a polymer (plastic) container which can be a flexible polymer container, such as a monobag, or a rigid or semi-rigid container, such as a polymer vial or bottle, including glass containers which have been coated with a polymer layer so as to avoid contact of the liquid contained with the glass. Said containers are composed wholly or in substantial portion of plastic materials which contain or are intended to contain a pharmaceutical formulation such as disclosed herein. In embodiments of the invention, the container has a fill volume of between about 20 and about 1000 mL. According to one embodiment of the invention, the medical product is provided in a concentration of SGP of from about 0.8 mmol/L to about 2.0 mmol/L in flexible polymeric bag having a volume of from about 50 mL to about 500 mL, preferably in a volume of from about 50 mL to about 300 mL, such as about 100 mL or about 250 mL.

As used herein, the "rigid" or "semi-rigid" containers which can be used in the context of the present invention refer to containers which are not squeezable (rigid) or squeezable (semi-rigid) and consist wholly or in part of a polymeric material which is in contact with the pharmaceutical composition. Rigid containers can be made from durable and lightweight PET plastics to heavy-duty HDPE. More options include PC, PETG, PP, LDPE or COP. These can appear in various shapes such as bottles or vials.

As used herein, the term "flexible container" refers to a container or bag made of a flexible material, such as bags made from plastic films. The term does not encompass polymeric rigid or semi-rigid containers. Using glass vials is discouraged because of the potential introduction of unwanted aluminum and other heavy metal ions which could potentially be released into the pharmaceutical composition.

Flexible containers or bags of the invention can be made of materials comprising, without limitation, polyvinyl chloride (PVC), polypropylene (PP), polyethylene (PE), ethylene vinyl alcohol (EVOH), ethylene-vinyl acetate (EVA) and all possible copolymers, essentially any synthetic material suitable for containing the components to be administered. Preferably, a flexible container according to the invention is made from a non-PVC material and/or does not contain DEHP.

Figure 2:
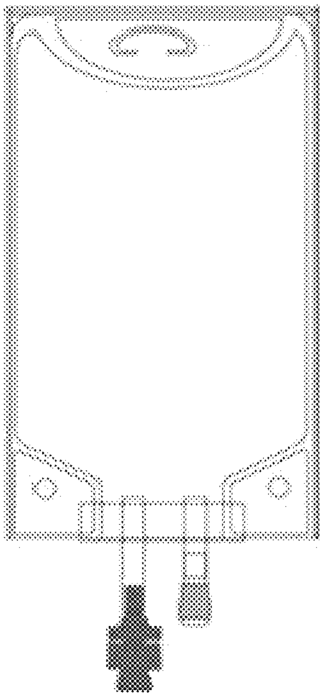
FIG. 2 is a schematic representation of a flexible single chamber container with one port tube.

According to one aspect of the invention, the disclosure provides for a flexible container, preferably a single-chamber container for pharmaceutical compositions according to the invention which may be prepared from any of the before-mentioned flexible films or materials. For example, the container may be in the form of a bag having one port tube only as the medical product according to the invention is generally not intended for direct administration but for use in the compounding of a parenteral nutrition formulation or for addition to a solution for intravenous infusion or to a ready-to-use or pre-mixed parenteral nutrition formulation (FIG. 2). Suitable containers, including soft bags, typically are sterile, non-pyrogenic, single-use, and/or ready-to-use. For example, the non-PVC and non-DEHP Viaflex or Viaflo containers (Baxter) can be used for accomplishing the present invention.

The pharmaceutical composition according to the invention is provided for administration to patients who require or should receive phosphate supplementation, including patients receiving parenteral nutrition. Specifically, the medical product is provided for administering phosphate to said patient, wherein the patient is an adult patient or a pediatric patient. According to yet another embodiment of the invention, the medical product is provided for preventing and/or treating phosphate deficiency in a patient, including patients receiving parenteral nutrition.

According to another embodiment of the invention, the pharmaceutical composition is for use in the compounding of parenteral nutrition formulations.

According to another embodiment of the invention, the pharmaceutical composition is used for supplementation of solution for intravenous injection or of ready-to-use parenteral nutrition products, such as, for example, multi-chamber bags having two, three, four or more chambers and comprising macronutrients such as amino acids, carbohydrates or lipids as well as, optionally, electrolytes and/or vitamins and/or trace elements. The medical product of the invention can be added to the solution for intravenous injection or to the parenteral nutrition product immediately before administration to the patient.

If not defined otherwise herein, all terms used in the context of the present invention are to be interpreted according to the understanding of a person skilled in the art.

EXAMPLES

The invention is further described by the following examples. These are not intended to limit the scope of the invention but represent preferred embodiments and/or certain aspects of the invention provided for greater illustration of the invention described herein.

Example 1: Synthesis of Sodium Glycerophosphate (a) Chemical Synthesis 26.1 g sodium phosphate monobasic (e.g. from Avantor), including 3.92 g water if the monohydrate is used, are provided at room temperature under nitrogen. 4 equivalents of glycerol, e.g. from P&G, (93.4 g or 74.9 mL) are added and rigorously stirred at a temperature of from 20° C. to 60° C. Then, 0.0385 equivalents of $H_3PO_4$ (85%), e.g. from CARLO ERBA Reagents, corresponding to 4.43 g of $H_3PO_4$ and 0.67 g of water are added at a temperature of below 70° C. under nitrogen. The mixture is heated to about 135° C. to 140° C. and then distilled under vacuum. The reaction is allowed to proceed for at least 20 hours. Afterwards, 130.6 mL of water are added at below 100° C. and the solution is stirred at high speed. 34.2 mL of 30.5% sodium hydroxide (e.g. from Merck), corresponding to 0.348 equivalents, are added during stirring. The pH should be between 12 and 13. The solution is then heated to between 95° C. and 100° C. The temperature is held for 2.5 to 3.5 hours. The yield of SGP is about 80.7% or higher.

(b) Crystallization 322.8 mL of the reaction mixture of (a) containing 250 g/L of sodium glycerophosphate which was filtered under nitrogen is provided in water and basified, if needed, with 33% (w/v) aqueous sodium hydroxide to a pH of 12.4. The solution is cooled to 10° C. under nitrogen. The temperature can be in a range of from 8° C. to 12° C. about 183 mL of ethanol are slowly added over 1.5 to 2.5 hours at a temperature of about 10° C., until a mixture of about 55% (v/v) of water in ethanol is obtained. After seeding (e.g. 0.40 g), the solution is kept at about 10° C. for about 12 hours followed by filtration and washing thrice with about 80 mL of 70% ethanol the crystals are dried under nitrogen at a temperature below 25° C., but temperatures of up to 30° C. do not create any issues. The yield is about 85%. The ethanol content is below 500 ppm.

The chemical structure of SGP, hydrated, can be confirmed by X-ray diffraction or proton and carbon-13 Nuclear Magnetic Resonance (NMR).

The SGP drug substance (hydrated) is packaged in a double low-density polyethylene bag (LDPE), and the double polyethylene bag is placed in a cardboard drum which is sealed with metal clamps.

(c) Pharmaceutical Composition

70% of the total WFI quantity needed was provided in a mixing tank. After reaching a temperature of 40° C. HCl 25% (4.9 mL/L) was added. After 10 min of agitation, SGP was added at 40° C. Then, WFI was added up to Q.S. and the solution was stirred at 40° C. for 30 min. Then the pH at 7.4. If needed a pH adjustment can be done by addition of HCl 0.5%. Then the solution was cooled down to 25° C. before it was transferred to the filling line, where the solution was filled into a flexible container, overpouched and sterilized.

Example 2: Determination of Alpha-Glycerophosphate, Beta-Glycerophosphate and Related Substances in Parenteral Nutrition Products by UPLC/CAD A study was performed to determine alpha-glycerophosphate, beta-glycerophosphate and related substances in different parenteral nutrition products. The quantification of related substances and of alpha- and beta-isomers of sodium glycerophosphate (α- and β-SGP) in sodium glycerophosphate raw material or products derived therefrom and the determination of chromatographic impurity in a β-SGP reference standard is done by HPLC/CORONA CAD.

In that method, DL-α-sodium glycerophosphate, β-sodium glycerophosphate, and SGP related substances are separated using ion exchange gradient HPLC on an anion exchange column. The SGP and the related substances are retained on the column and separated by differential ionic interaction with the column packing. The analytes are detected by Corona CAD (charged aerosol detector) by the following steps: nebulization of the eluent from the column; evaporation of the solvent from the aerosol; charging of the solid particles; monitoring the charged particles. For the method it is possible to use, for example, High Performance Liquid Chromatography (HPLC) systems (e.g., Alliance 2695) or Ultra Performance Liquid Chromatography (UPLC) systems (e.g., Waters Acquity) used in HPLC mode; an auto sampler and injection system able to deliver 50 μL; a column oven able to work at 30° C.; a Corona CAD detector; an analytical column such as a Hamilton PRP-X100 Anion Exchange column, 5 μm particle size, 250 mm length×4.6 mm. Channel A: purified water; Channel B: 5 mM ammonium formate as mobile phase 1; Channel C: 200 mM ammonium formate buffer, pH 3.70 as mobile phase 2; Channel D: H2O/MeOH 50/50. Total flow is about 1 L/min, gas pressure 35 psi, current (initial) is ≤0.4 pA, flow rate (mL/min) is about 1, column temperature 30° C. The relative retention time for each peak including phosphoric acid, alpha- and beta-SGP and SGP-related products is shown in Table III.

TABLE III

Relative retention time for the peaks relating to phosphoric acid, alpha- and beta-SGP and SGP-related products. RRT refers to "relative retention time"

| Peak | Approximate RRT |
|---|---|
| Phosphoric acid | 0.8 |
| α-SGP | 0.9 |
| β-SGP | 1.0 |
| DGP-1 (Diglyceryl Phosphate isomer 1) | 1.1 |
| DGP-2 (Diglyceryl Phosphate isomer 2) | 1.3 |
| TGP (Triglyceryl Phosphate isomers) | 1.6 to 1.8 |
| GDP-1 (Glyceryl Diphosphate isomer 1) | 2.4 |
| GDP-2 (Glyceryl Diphosphate isomer 2) | 2.5 |
| TGDP-1 (Triglyceryl Diphosphate isomer 1) | 2.7 |
| TGDP-2 (Triglyceryl Diphosphate isomer 2) | 2.9 |
| DGTP (Diglyceryl Triphosphate) | 3.6 |

According to the above, a sodium glycerophsophate according to the invention (Example 1) was provided in a 30% (w/v) solution. The pH was adjusted to physiological pH (7.4) using 30% HCl. The solution was filled in 100 mL monobags and sterilized. The samples were analyzed before and after sterilization and after T3M storage at 40° C. and 5° C. Glycophos® was analyzed in the same way for comparison. The results are summarized in Table IV.

TABLE IV

Determination of alpha-glycerophosphate, beta-glycerophosphate and related substances in parenteral nutrition products by UPLC/CAD

| % of total phosphate | SGP (invention) before sterilization* | SGP (invention) after-sterilization | SGP (invention) T3M at 5° C./NMT 25% RH | SGP (invention) T3M at 40° C./NMT 25% RH | GLYCOPHOS |
|---|---|---|---|---|---|
| Phosphoric acid | 0.31 | 0.37 | 0.78 | 1.13 | 1.85 |
| alpha-SGP | 39.75 | 39.41 | 40.01 | 39.85 | 34.55 |
| beta-SGP | 48.68 | 48.03 | 48.91 | 48.60 | 36.24 |
| DGP-1 | 1.80 | 1.83 | 1.49 | 1.45 | 4.50 |
| DGP-2 | 0.91 | 0.93 | 0.63 | 0.67 | 2.57 |
| GDP-1 | 3.81 | 3.74 | 3.40 | 3.43 | 8.32 |
| GDP-2 | 4.74 | 4.69 | 4.80 | 4.82 | 11.30 |
| TGDP-1 | not detected | 0.04 | not detected | not detected | not detected |
| TGDP-2 | not detected | not detected | not detected | not detected | not detected |
| DGTP | not detected | 0.15 | not detected | not detected | 0.67 |
| Sum of alpha-SGP + beta-SGP | 88.43 | 87.44 | 88.93 | 88.53 | 70.80 |
| Sum of SGP related substance (without phosphoric acid) | 11.26 | 11.38 | 10.32 | 10.37 | 27.36 |
| alpha-SGP/beta-SGP ratio | 0.79 | 0.80 | 0.82 | 0.83 | 1.01 |

*corresponding to raw material/pharmaceutical drug product

Accordingly, it was found that the content of phosphoric acid, individual related substances and the total related substances observed in the medical product according to the invention is very low, and lower in comparison to the prior art product which was used for comparison. The study also showed that the free phosphate content of the medical product increased after sterilization, but that after T3M of storage at 40° C./NMT 25% RH, it does not show an increase. Moreover, in the samples stored at 5° C. again have a lower free phosphate content compared to the sample kept at 40° C.

Regarding the ratio of alpha-SGP and beta-SGP, it was found that the medical product according to the invention tends to comprise more beta-SGP than alpha-SGP. Without wanting to be bound by theory, this may be a result of the production process of SGP as described above.

Example 3: Determination of Aluminum Content

The aluminum determination analysis is performed by Inductively Coupled Plasma Mass Spectrometry (ICP-MS). Inductively Coupled Plasma Mass Spectrometry (ICP-MS) is a type of mass spectrometry that is highly sensitive and capable of the determination of a wide range of metals at trace levels (one part per billion (ppb) level). It is based on the combination of an inductively coupled plasma as a method of producing ions with a mass spectrometer as a method of separating and detecting the ions.

In the ICP, a solution is introduced into an argon plasma as aerosol droplets. The high temperature plasma dries the aerosol and dissociates the molecules which are then decomposed into excited atoms and ions. The ions are directed into the MS. The detector rapidly scans the mass range. At any given time, only one mass-to-charge ratio will be allowed to pass through the mass spectrometer from the entrance to the exit. This allows separation of the tested ions. Upon exiting the mass spectrometer, the ion strikes an electron multiplier, which serves as a detector. The ICP-MS can determine aluminum against a calibration curve, constructed using standard solutions of the analyte. Equivalent equipment may be used. Quantities proportionally larger or smaller that the specified volumes of samples and reagents may be used. Subsequent steps, such as dilution, may be adjusted accordingly to yield to concentrations equivalent to those specified. As required, calculation of results may be corrected to account for changes in volumes.

Materials include a diluent which is prepared from 5% nitric acid and 2% hydrochloric acid and adding purified water in appropriate proportions after mixing. 1.0 ng/mL and 50 ng/mL calibration standards in diluent are prepared using Al stock standard material. The diluent is used as blank solution Drift check solution consists of 25 ng/mL in diluent using Al stock control material.

The analysis is done with standards and samples. A linear regression will be calculated by the software using blank and the calibration standards. The sample concentration will be calculated by the instrument software, taking into account the dilution factor of the sample introduced in the sequence of analysis. Correction with internal standard will be performed by the instrument software for all solutions. Drift check solution are analysed after the calibration standards, periodically during the analytical run and at the end of the analytical run. If the test solution concentration is lower than or equal to the QL (quantitation limit), the data is reported as not more than the QL. If the test solution concentration of the test solution is higher than the QL, the calculated content is reported.

Example 4: Determination of Free Phosphate

Free phosphate is complexed by ammonium vanadate and ammonium molybdate into a phosphate-vanado-molybdate complex of yellow color. The absorbance of said complex at a wavelength of 405 nm is directly proportional to the analyte content. For example, a UV-Visible Spectrophotometer from Perkin-Elmer Lambda 25 can be used for the measurement together with 2.5 ml cuvettes. Purified water (Milli-Q) is used for the analysis. Ammonium heptamolybdate, $4H_2O$ can be obtained from Merck (Ref 1.01182), ammonium vanadate (V) with a purity ≥99.0% can be obtained from Sigma Aldrich (Ref 398128). Further, nitric acid 69% (Merck, Ref 1.01799) and sodium phosphate (Aldrich, Ref 342483) are required.

The vanado-molybdate reagent is prepared by adding 2 g of ammonium heptamolybdate, $4H_2O$, and 0.100 g of ammonium vanadate (V) to 50 mL of purified water in a 100 mL volumetric flask. The solution is mixed and kept at 70° C. for 30 minutes in order to fully dissolve the reagents. The solution is again mixed and allowed to cool to room temperature. Then, 14 mL of nitric acid 69% are added to the flask, followed by mixing and cooling to RT. The solution is filled up to volume with purified water and thoroughly mixed. The solution should be prepared on the day of its used and should not be stored. The Blank solution is purified water. The Blank is analyzed after application of the complexing process.

For the Stock calibration solution, between 31.5 mg and 38.5 mg of sodium phosphate ($Na_3PO_4$) are accurately weighed into a 100 mL volumetric flask and dissolved and diluted to volume with purified water. The solution is mixed to obtain the $SM_{PO4}$ solution at 0.2 mg/ml in phosphate content. The phosphate concentration in the $SM_{PO4}$ solution can be calculated as follows:

$$C_{PO4}(\text{mg/ml}) = \frac{\text{Weight } Na_3PO_4(\text{mg})}{\text{Dilution volume (mL)}} \times \frac{\text{Molecular weight } PO_4(\text{g/mol})}{\text{Molecular weight } Na_3PO_4(\text{g/mol})} \times \frac{\text{Purity } Na_3PO_4(\%)}{100},$$

wherein the molecular weight of PO4 is 94.94 g/mol and the molecular weight of $Na_3PO_4$ is 163.94 g/mol.

Sample solution are prepared by weighing in between 225 and 275 mg of a test sample into a 25 mL volumetric flask. After dissolving the sample, the solution is diluted to volume with purified water and thoroughly mixed. The sample solution is then analyzed according to the complexing process, which should be carried out in the order in which the samples solutions have been prepared, including adhering to the same time intervals so as to avoid any false results.

Said complexing process is carried out by combining 20 mL of the solution (Sample, Blank or Calibration solution as required) and 5 mL of the vanado-molybdate reagent. The solution should not be stored but instead be processed immediately. The solutions are allowed to react for 30 minutes after the addition of the vanado-molybdate reagent before the absorbance measurement.

The invention claimed is:

1. A pharmaceutical composition comprising sodium glycerophosphate (SGP) in a concentration of from about 0.5 mmol/mL to about 30.0 mmol/mL, wherein
   - (a) the amount of free phosphate is below 5% (w/w) of the total phosphate,
   - (b) the total amount of SGP related substances is below 15% (w/w) of the total phosphate, and
   - (c) the amount of aluminum is below 500 ppb.

2. The pharmaceutical composition according to claim 1, wherein the ratio of alpha sodium glycerophosphate (α-SGP) and beta sodium glycerophosphate (β-SGP) is from about 1:5 to about 5:1.

3. The pharmaceutical composition according to claim 1, wherein the pH is from about 5.0 to about 8.0.

4. The pharmaceutical composition according to claim 1, wherein the composition is provided in a polymeric container.

5. The pharmaceutical composition according to claim 1, wherein the composition is terminally heat-sterilized.

6. The pharmaceutical composition according to claim 1, wherein the SGP related substances in the pharmaceutical composition are selected from the group consisting of glycerodiphosphate (GDP), diglycerophosphate (DGP), triglycerophosphate (TGP), diglycerodiphosphate (DGDP), triglycerodiphosphate (TGDP), cyclic glycerodiphosphate (CGDP), and diglycerotriphosphate (DGTP).

7. The pharmaceutical composition according to claim 1, wherein the pharmaceutical composition is stable at a temperature of from about 1° C. to about 25° C. for at least 12 months.

8. The pharmaceutical composition according to claim 1 for the administration of phosphate to a patient.

9. The pharmaceutical composition according to claim 1 for prevention or treatment of phosphate deficiency in a patient.

10. The pharmaceutical composition according to claim 8, wherein the patient is a patient receiving parenteral nutrition.

11. The pharmaceutical composition according to claim 1, wherein the patient is an adult or a pediatric patient.

12. The pharmaceutical composition according to claim 1 for use in the compounding of a parenteral nutrition formulation.

13. The pharmaceutical composition according to claim 1 for addition to a ready-to-use parenteral nutrition product or a solution for intravenous injection.

14. A method of preparing a pharmaceutical composition according to claim 1 comprising the steps of:
   - (a) Dissolving an SGP drug product in water to form a SGP solution for injection under pH control;
   - (b) Adjusting the pH of the SGP solution to a value of from about 6.8 to about 7.8, preferably with hydrochloric acid;
   - (c) Filling the SGP solution into a polymeric container;
   - (d) Overpouching the filled and sealed container; and
   - (e) Sterilizing SGP solution in the container before or after step (d);

wherein the SGP drug product used comprises not more than 500 pbb of aluminum, not more than 15% (w/w) of SGP related substances and not more than 5% (w/w) of free phosphate.

15. A method of preparing a sodium glycerophosphate drug product for use in the production of a pharmaceutical composition according to claim 1 comprising the steps of:
   - (a) reacting a mixture of phosphoric acid and sodium phosphate, preferably at a ratio of about 20:80, with glycerol at a temperature of from about 130° C. to about 150° C. to form a reaction mixture;
   - (b) distilling off water which is generated during the reaction from the reaction mixture;
   - (c) saponifying, preferably at a pH of between about 12 and about 13, and maintaining the reaction mixture at about 90° C. to 110° C. for about 2 to 5 hours;
   - (d) crystallizing the sodium glycerophosphate by precipitation from a solution of the reaction mixture comprising the sodium glycerophosphate in water and ethanol; and optionally
   - (e) drying the sodium glycerophosphate.

16. The method according to claim 15, wherein the reaction of step (a) is done with monobasic sodium phosphate and wherein glycerol is added at 3 to 6eq.

17. The method according to claim 15, wherein the saponification of step (c) is done with sodium hydroxide, preferably with about 0.3 to about 0.4 equivalents.

18. The method according to claim 15, wherein the crystallization of step (d) is performed at a temperature of from about 1° C. to about 20° C.

19. A sodium glycerophosphate (SGP) drug product, wherein the SGP drug product is produced according to claim 15, and the total amount of SGP related substances is below 15% (w/w) of the total phosphate in the SGP drug product.

20. A sodium glycerophosphate (SGP) drug product, wherein
   - (a) the amount of free phosphate in the drug product is not more than 5% (w/w) of the total phosphate,
   - (b) the total amount of SGP-related substances in the drug product is not more than 15% (w/w) of the total phosphate, and
   - (c) the amount of aluminum in the drug product is not more than 500 ppb.

21. The pharmaceutical composition according to claim 1, wherein the pharmaceutical composition is stable at a temperature of from about 1° C. to about 25° C. for at least 18 months.

22. The pharmaceutical composition according to claim 1, wherein the pharmaceutical composition is stable at a temperature of from about 1° C. to about 25° C. for at least 24 months.

23. The pharmaceutical composition according to claim 1, wherein the amount of aluminum is below 250 ppb.

24. The pharmaceutical composition according to claim 1, wherein the amount of SGP related substances is below 12% (w/w) of the total phosphate.

25. The SGP drug product according to claim 19, wherein the SGP related substances are selected from the group consisting of glycerodiphosphate (GDP), diglycerophosphate (DGP), triglycerophosphate (TGP), diglycerodiphosphate (DGDP), triglycerodiphosphate (TGDP), cyclic glycerodiphosphate (CGDP), and diglycerotriphosphate (DGTP).

26. The SGP drug product according to claim 20, wherein the SGP related substances are selected from the group consisting of glycerodiphosphate (GDP), diglycerophosphate (DGP), triglycerophosphate (TGP), diglycerodiphosphate (DGDP), triglycerodiphosphate (TGDP), cyclic glycerodiphosphate (CGDP), and diglycerotriphosphate (DGTP).

27. The SGP drug product according to claim 20, wherein the ratio of alpha sodium glycerophosphate (α-SGP) and beta sodium glycerophosphate (β-SGP) is from about 1:5 to about 5:1.

* * * * *